United States Patent [19]

Uda et al.

[11] Patent Number: 4,776,911
[45] Date of Patent: Oct. 11, 1988

[54] ELASTICIZED UNIT, APPARATUS FOR MAKING THE ELASTICIZED UNIT, GARMENTS INCORPORATING THE UNITS, AND METHOD FOR MAKING THE GARMENT

[75] Inventors: Masashi Uda, Minoo; Jun Oohira, Kagawa, both of Japan

[73] Assignee: Toyo Eizai Kabushiki Kaisha, Kawanoe, Japan

[21] Appl. No.: 68,222

[22] Filed: Jun. 30, 1987

[30] Foreign Application Priority Data

Jun. 30, 1986 [JP] Japan .................................. 61-153660
Nov. 11, 1986 [JP] Japan .................................. 61-269423
Feb. 13, 1987 [JP] Japan .................................. 62-31958

[51] Int. Cl.⁴ ............................................ B65H 81/00
[52] U.S. Cl. .................................... 156/161; 156/164; 156/229; 156/267

[58] Field of Search ............... 156/161, 164, 176, 177, 156/178, 179, 229, 250, 267; 604/385.1, 385.2

[56] References Cited

U.S. PATENT DOCUMENTS 4,601,717  7/1986  Blevins .......................... 604/385.1
4,626,305 12/1986  Suzuki et al. ................... 156/164
4,681,579  7/1987  Toussant et al. ................ 604/385.1
4,687,477  8/1987  Suzuki et al. .................. 604/385.1

Primary Examiner—Michael W. Ball
Assistant Examiner—David Herb
Attorney, Agent, or Firm—Oblon, Fisher, Spivak, McClelland & Maier

[57] ABSTRACT

An elasticized fabric unit comprising a pair of tape members spacedly provided, and a plurality of elastic strands fixed to the tape members at their opposite ends, and a garment incorporating the elasticized unit, an apparatus for making the elasticized units, a method for incorporating the elasticized units in the garment.

2 Claims, 9 Drawing Sheets

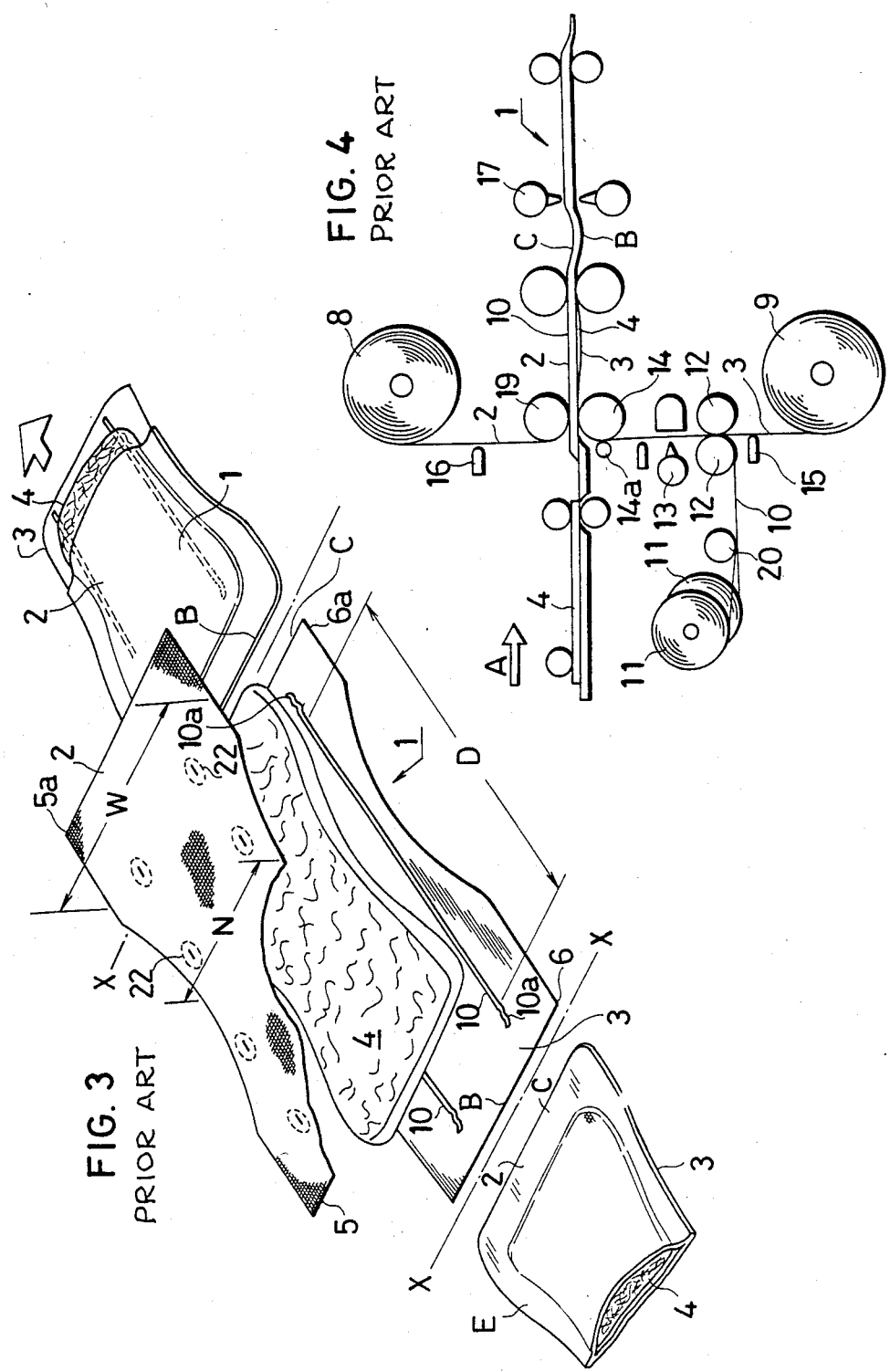

ELASTICIZED UNIT, APPARATUS FOR MAKING THE ELASTICIZED UNIT, GARMENTS INCORPORATING THE UNITS, AND METHOD FOR MAKING THE GARMENT

BACKGROUND OF THE INVENTION

1. Field of the Invention

The present invention relates to an elasticized unit, apparatus for making such units, garments incorporating the units, and methods for making such garments. Herein the elasticized unit means a unit containing a plurality of elastic strands providing a sealed tight fit so as to avoid the leakage of body excrement.

2. Description of the Prior Art

In underwear, especially baby's diapers and female napkins, elasticity is essential for providing a sealed tight fit between the skin and the fabric. For securing the elasticity, elastic strings are used around the leg or waist area of the wear, and the wearer fastens the string after he puts it on. Alternatively, when the wearer puts it on, the strings naturally tighten to the skin. The strings are fixed to the garment by stitches or by melting or bonding. The fixing work is labor and time consuming, thereby leading to a high production cost.

To save cost the stitching method is generally avoided and the melting or bonding (with an adhesive) method is commonly adopted. Under the known methods a problem is that the fabric of the garment and the elastic material, such as strings, have different elasticity. In fixing elastic strings, the base material of the garment is stretched to its own full extent, and allowed to contract after the strings are fixed. However it is difficult to fix the elastic strings to the stretched fabric. To overcome the difficulty experience and skill is required.

To facilitate the fixing work many proposals have been made but they are not satisfactory in efficiency and cost.

To explain the background of the present invention reference will be made to FIG. 3, which is a perspective view showing a known disposable diaper, partly broken to show the internal structure. The diaper 1 is made up of a permeable nonwoven sheet 2 and a sealing sheet (e.g. a plastic film) 3 overlaid with an absorbent sheet 4 having a smaller area than the sheets 2 and 3. The sheets 2 and 3 are thermally jointed to each other at their peripheries C. The reference numeral 10 denotes an elastic string provided in its stretched state along the opposite side margins of the sealing sheet 3.

The diaper shown in FIG. 3 is produced in the manner shown in FIG. 4:

The permeable sheet 2 is supplied onto the absorbent sheet 4 from a first roll 8, and the sealing sheet 3 is supplied to the under-surface of the absorbent sheet 4 from a second roll 9. These sheets 3 and 4 are pressed and laminated at 22 by a pair of rollers 14, 19. The reference numerals 15 and 16 denote nozzles through which an adhesive is preliminarily coated on the sheets 2 and 3. An elastic strand 10 is supplied from rollers 11, and adhered to sheet 3 in its stretched state. The laminated sheet is appropriately trimmed, and finally cut to desired lengths at 17. In this way a disposable diaper shown in FIG. 3 is produced. The reference numeral 13 denotes a heater whereby the elastic strand is thermally cut.

In using this diaper the permeable sheet 2, especially a narrow portion (N), is kept in contact with the baby's crotch, and a wide portion (W) is kept in contact with his belly and back. The corners 5 and 5a, 6 and 6a of the diaper 1 are releasably fixed to each other by adhesive tapes.

In this way the sealed tight fit between the cloth and the skin of the baby is secured. In the method mentioned above the elastic strands 10 are arranged in the direction in which the sealing sheet 3 runs, thereby keeping the strands in their stretched state while the sheet 3 is running. This may be advantageous but when it is cut it often happens that the adhesive in the part 10a near the cut still remains too fluid to fix to the sheet. This part tends to become separated from the sheet during use. To avoid this problem a special kind of adhesive is used or the amount of the adhesive is increased. Nevertheless the bond between the sheet and the elastic strands becomes poor.

The leakage of body excretion also occurs through the waist area of the diaper, so that it is required for the cloth to fit the baby's belly and back areas. Normally the diaper is made so as to tighten the fabric around them but that part which keeps contact with the skin tends to become loose over a period of use, thereby causing a gap between the skin and the cloth. The loose diaper often occurs as a result of babies' action. The disposable diapers have the difficulties pointed out above, that difficulty is in the production, and in the maintenance of the sealed tight fit for the skin.

OBJECTS AND SUMMARY OF THE INVENTION

The present invention aims at overcoming the difficulties encountered by the known disposable garments, and has for its object to provide an elasticized fabric unit capable of easy and economical production, and of ready incorporation in garments.

According to one aspect of the present invention there is provided an elasticized fabric unit, which comprises a pair of mutually spaced tape members, and a plurality of elastic strands fixed to the tape members at their opposite ends.

According to another aspect of the present invention there is provided an apparatus for making elastic fabric units, the apparatus comprising a pair of conveyors having a plurality of engagement means thereon for elastic strands; a rotative arm for winding the strands around the conveyors; and means for fixing a predetermined number of strands to tape members.

According to a further aspect of the present invention there is provided a garment for providing a sealed tight fit between the skin and the fabric, the garment comprising a base fabric material; an elasticized fabric unit comprising a pair of tape members and a plurality of elastic strands fixed to the tape members; the elasticized fabric unit being fixed to the base material with the elastic strands being in their stretched state.

According to a still further aspect of the present invention there is a method of incorporating elastic strands in the garment, the method comprising coating an adhesive on a base material of the garment in conveyance so as to form adhesive zones at certain intervals; fixing elastic strands in their stretched state to the base material, wherein the elastic strands are caused to advance at controlled intervals in the moving direction of the base material; and cutting the base material incorporating the elastic units to a predetermined length.

Other features of the invention will become apparent in the course of the following descriptions of exemplary embodiments which are given for illustration of the invention and are not intended to be limiting thereof.

BRIEF DESCRIPTION OF THE DRAWINGS

FIG. 3 is a perspective view, partly broken, showing a known disposable diaper;

FIG. 4 is a diagrammatic view exemplifying a known method for making a disposable diaper;

DETAILED DESCRIPTION OF THE PREFERRED EMBODIMENTS

In FIG. 1(a) there is provided a pair of tape members 36, 36a and 37, 37a, each pair of tape members being mutually bonded and spaced from each other with four elastic strands (E) interposed therebetween. The terminating ends of each strand are inserted and bonded in between the tape members 36 and 36a, and 37 and 37a. In this way the tape members and strands are unified into a unit. The tape members and strands can be thermally joined to each other or alternatively they can be stitched.

FIG. 1(b) shows that at least one of the tape members is longer than the other, wherein the adhesive surfaces (S) of the longer tape members are exposed as shown in FIG. 1(b). These protruded portions can be used to allow other units to be adhered thereto. In this way the elastic unit is produced, but to strengthen the unit at least one resilient member can be provided alongside the topmost strand unit. In this case the resilient member is desirably thin, otherwise it would negate the elasticity of the strands. Preferably the resilient member is a permeable resilient sheet, such as a nonwoven fabric.

Figure 1:
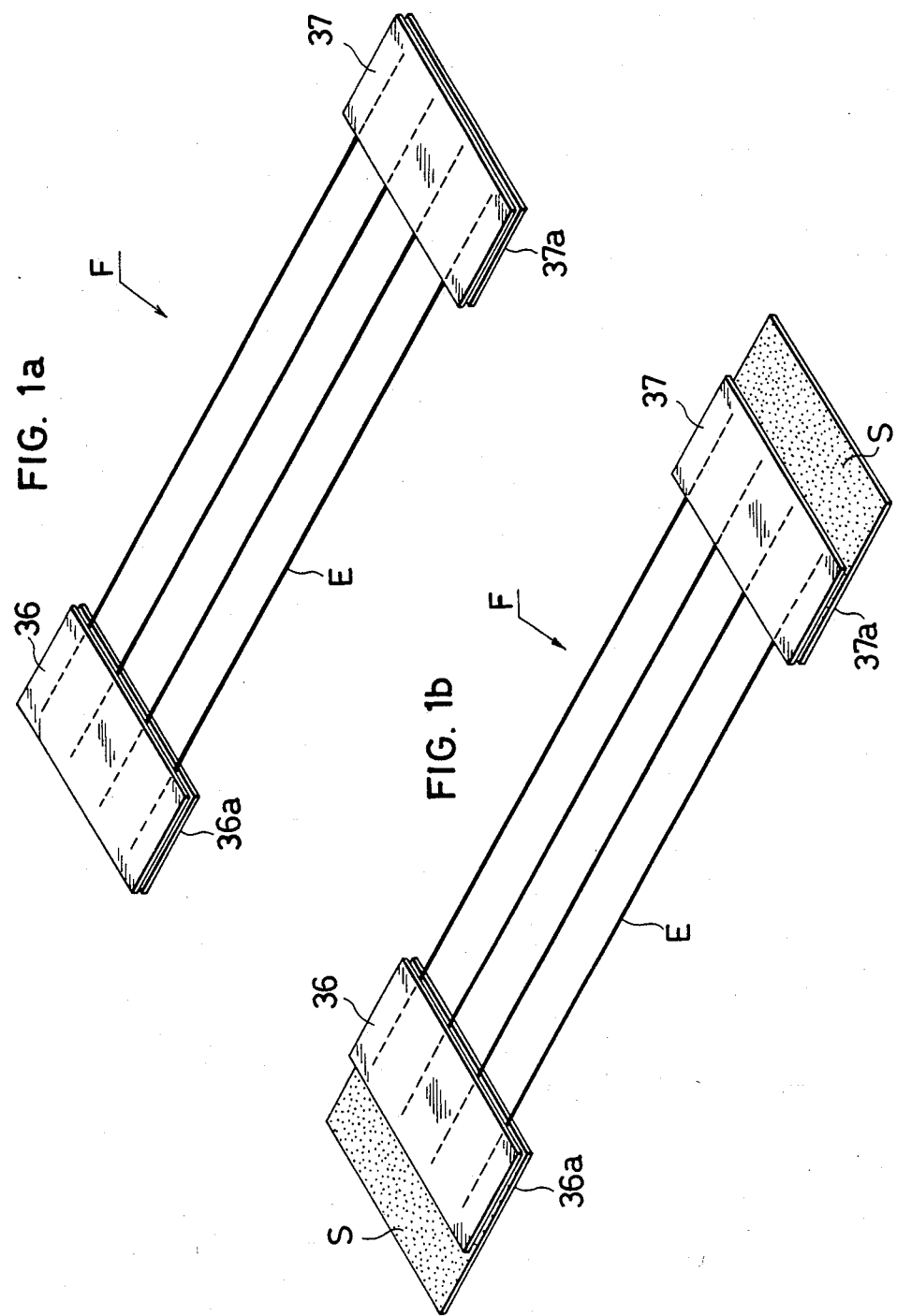
FIGS. 1 are perspective views showing examples of an elasticized fabric unit.
Figure 2:
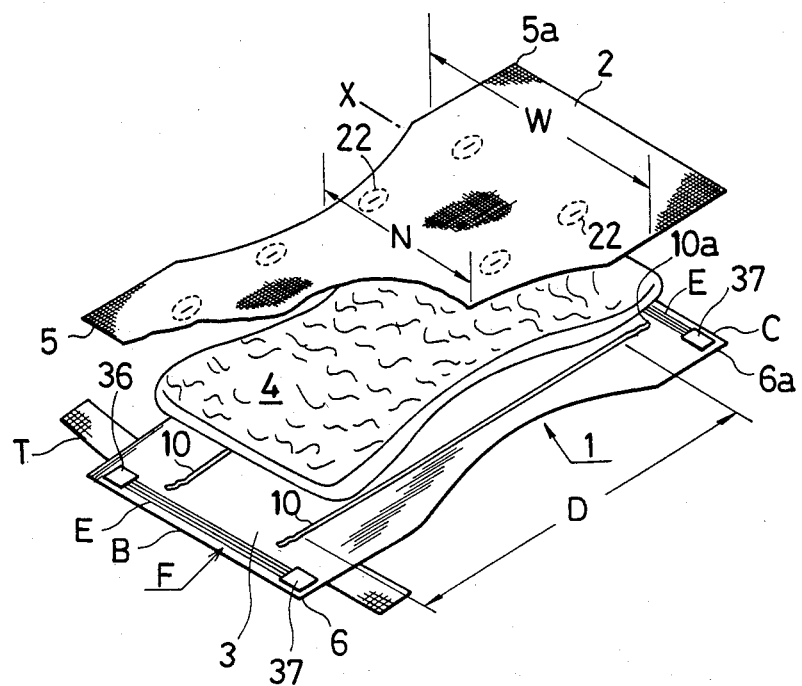
FIG. 2 is a perspective view showing a disposable diaper incorporating the elasticized units of FIG. 1.

Referring to FIG. 2 a disposable diaper incorporating the elasticized units shown in FIG. 1 will be described:

The finished elasticized units (F) are fixed to the opposite ends of a sealing sheet 3. In the drawings the components other than the units (F) are the same as those shown in FIG. 3, and denoted by like reference numerals. The units (F) are effective to give gathered effects to the garment (diaper).

The diaper is put on the baby's body by means of a fastener tape (T).

In the illustrated embodiment the strands are sufficiently spaced to secure an increased permeability as compared with the case where a wide elastic band is used under the known method. Permeability is essential for protecting the skin against confined moisture. The use of the elasticized unit (F) avoids such problems due to the confined moisture which often occurs in the known elastic bands. The illustrated example is a disposable diaper but the elasticized units of the present invention can be applied to garments other than diapers; for example, women's napkins, ordinary underwear or materials for industrial use which require gathered effects.

When the elasticized units are fixed to the sealing sheet 3 it is possible to fix them over the entire surface thereof or at certain intervals. The latter will increase the folds on the sealing sheet, thereby giving better gathered effects.

Figure 5:
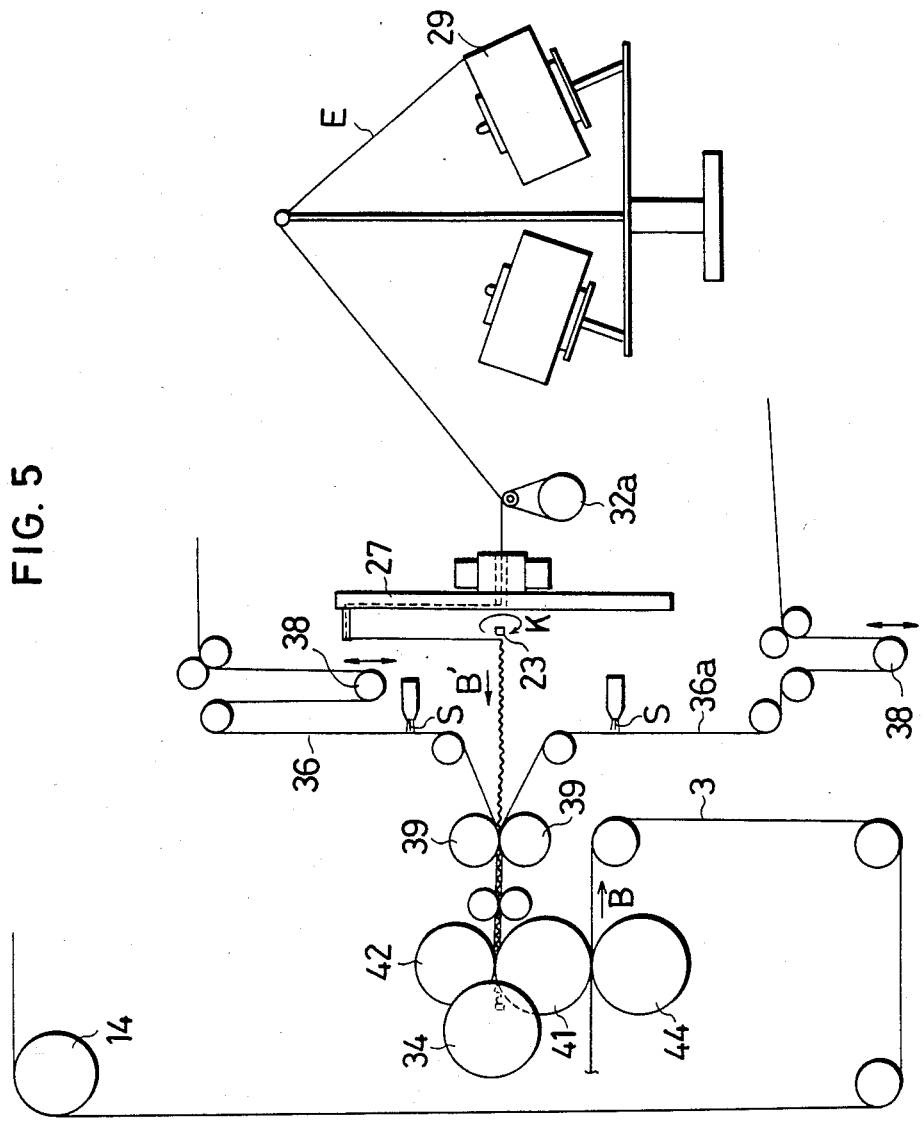
FIG. 5 is a diagrammatic view exemplifying a method for making a disposable diaper according to the present invention.
Figure 6:
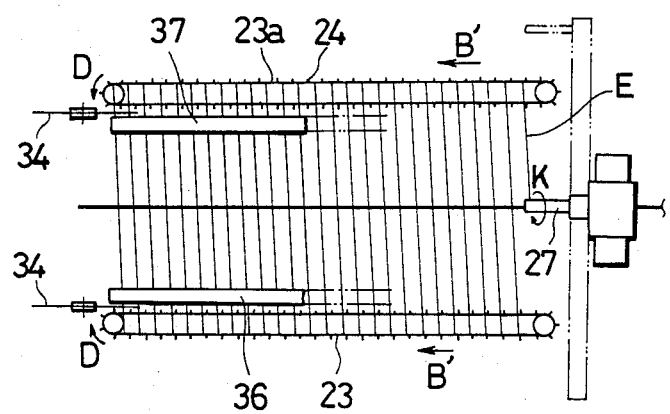
FIG. 6 is a plan view showing a main part of the arrangement shown in FIG. 5.

Referring to FIGS. 5 and 6 there is provided a winder 29 for winding elastic strands (E) thereon. Tape members 36, 36a and 37, 37a are supplied onto the elastic strands (E). As shown in FIG. 6 there is provided a pair of conveyor belts 23, 23a above the sealing sheet 3, which belts run in parallel with but in the opposite direction (B') to the running direction (B) of the sealing sheet 3. The conveyor belts 23, 23a are provided with pins 24 at given spaces, whereby the elastic strands are spaced one from another. The elastic strands (E) are supplied from the winder 29 through a tension roller 32a to a rotary arm 27, where the strands (E) are led to an outlet of the arm 27. The arm 27 is rotated in the direction of arrow (K) about the belts 23, 23a which rotate in the direction of arrow (D) and move in the direction of arrow (B') (FIG. 6). In this way the strands (E) are wound along an orbit around the belts 23 and 23a.

The tape members 36 and 37 are supplied from a group of rollers including a pair of main rollers 38, through which the tape members are stretched as desired. Then an adhesive is coated in the inner surface of the tape members 36, 37. The tape members and the strands are pressed by press rollers 39, thereby securing the bond therebetween. Instead of supplying the tape members in the moving direction of the strands, it is also possible to cover the whole of the strands with a wider cloth material supplied from the sides of the wound strands; that is, from the direction perpendicular to the moving direction of the strands. In this case the opposite edges of the material are bonded to the strands.

Finally the wound strands are cut into units of a desired length by a cutter unit 34.

Figure 7:
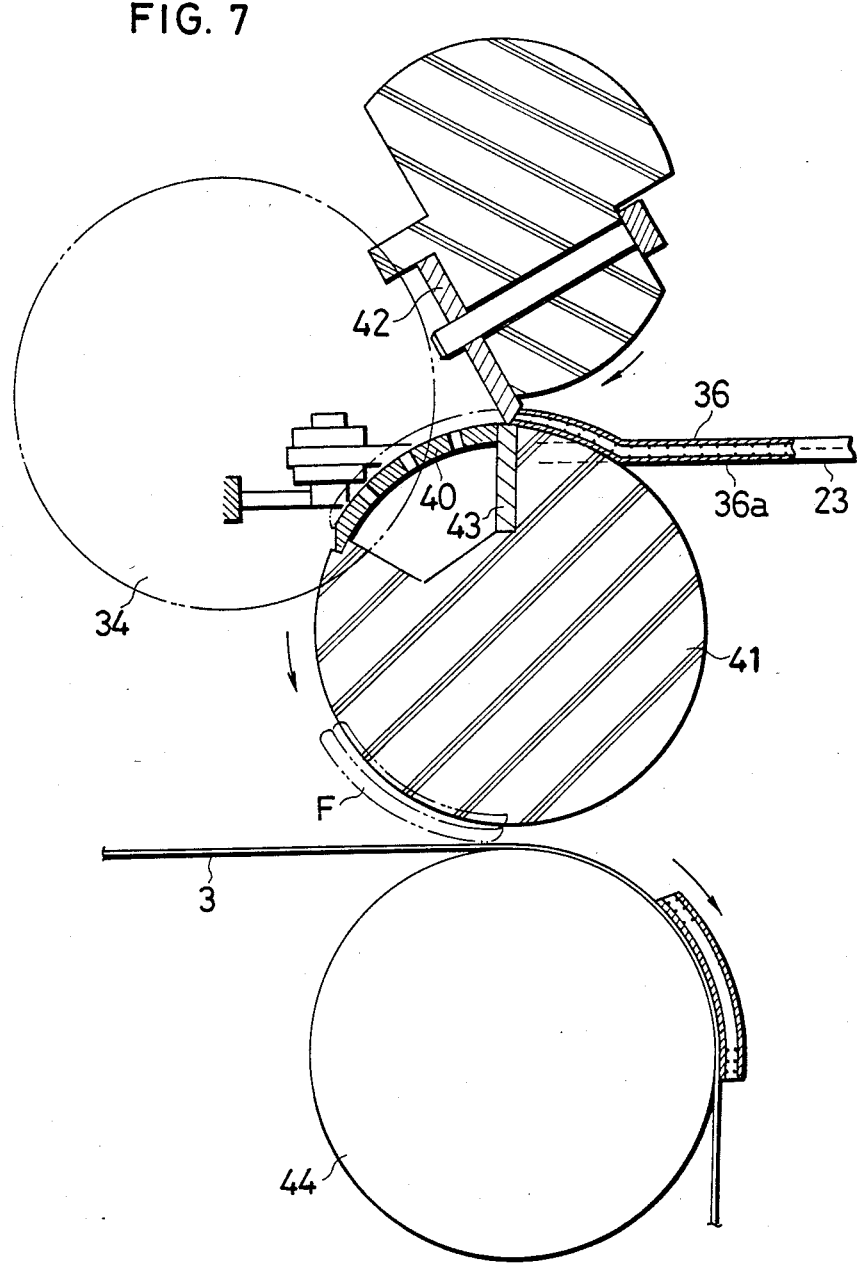
FIG. 7 is a schematic view showing the cutting section shown in FIG. 5.

Referring to FIG. 7 the cutter unit 34 will be described:

There is provided a roller 41 which has a lid 40 covering a recess produced in the periphery thereof. The lid 40 has several sucking apertures. The reference numerals 42 and 43 denote an upper blade 42 and a lower blade 43. The upper blade 42 rotates into contact with the lower blade 43, during which the tape members and strands are cut. The rotating speed of the roller 41 is varied. Beginning when the starting portion (left-hand portion) of the lid 40 is located in opposition to the upper blade 42, up to when the lower blade 43 is located in opposition therewith as shown in FIG. 7, the roller 41 rotates at the same speed as that of the belts 23, 23a.

After the cutting is finished with the lower blade 43 having passed the upper blade 42, the roller 41 accelerates up to when the lid 40 comes to the position indicated by phantom lines. From there the roller 41 rotates synchronously with the running speed of the sealing sheet 3 until the elastic unit (F) is delivered thereto. After the delivery is finished the roller 41 accelerates until the starting portion of the lid 40 returns to the position in opposition with the upper blade 42.

When the elastic strands (E) are conveyed by the belts 23, 23a, and placed on the lid 40 it is sucked via suction applied through the apertures, thereby to secure the strands (E). At this stage a side cutter 34 is moved toward the strands (E), and cuts both ends thereof. The roller 41 rotates up to the position shown in FIG. 7, and at the same time the upper blade 42 rotates in the clockwise direction. In this way the elastic strands (E) fixed to the tape members 36, 37 are cut into a finished elastic unit (F), which is then conveyed by the suction supplied through the apertures in the lid 40 up to the position indicated by the phantom lines on the roller 41, where the elastic unit (F) is fixed to the adhesive surface of the sealing sheet 3 which is conveyed by the roller 44. At this moment the elastic unit (F) is released from the suction through the apertures in the lid 40. The roller 41 returns to the starting position for the subsequent operation.

Figure 8:
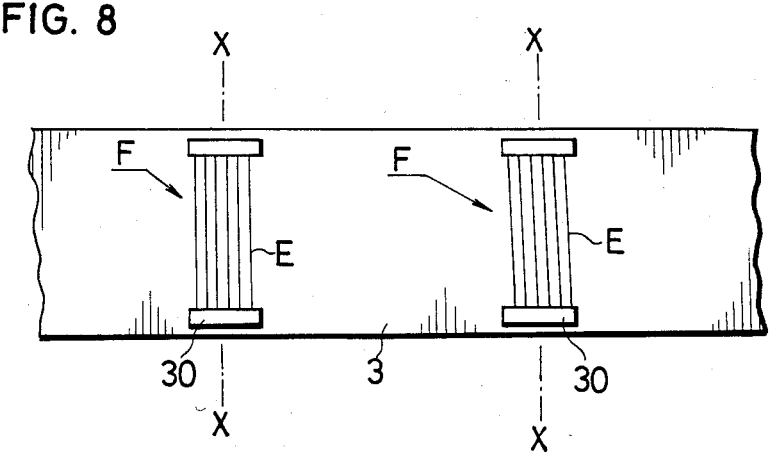
FIG. 8 is a plan view showing an example of the state in which the elasticized units are attached to the sealing sheet.

FIG. 8 shows the state in which the finished elastic units (F) are fixed to adhesive-coated zones on the sealing sheet 3. The sealing sheet 3 having the elastic units (F) thereon is conveyed to between the rollers 14 and 19 shown in FIG. 4. The number of the elastic units (F) can be selected as desired. Preferably two to five elastic units are used.

Figure 9:
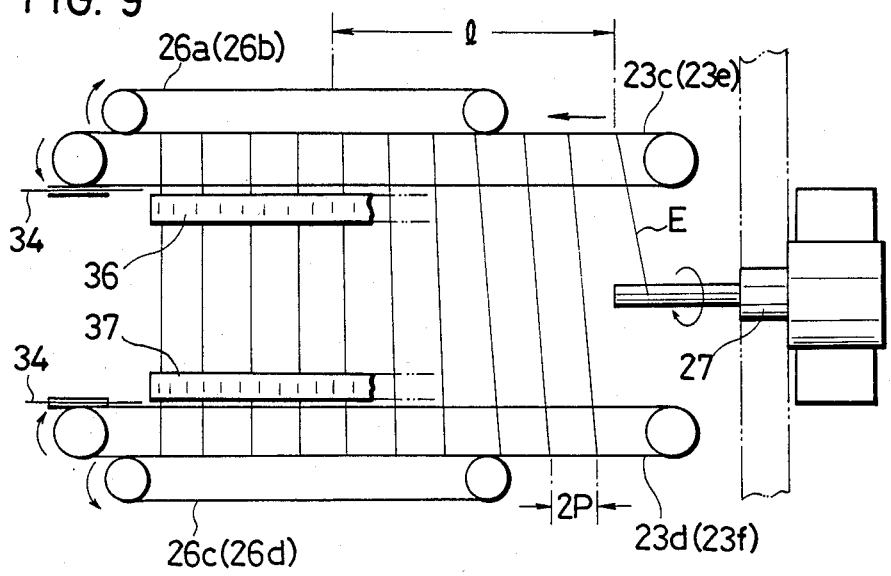
FIG. 9 is a diagrammatic plan view showing a modified version of the arrangement for carrying out the present invention.
Figure 10:
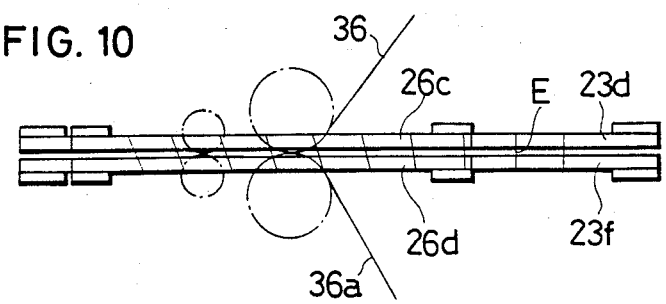
FIG. 10 is a diagrammatic side view of the arrangement of FIG. 9.

As shown in FIG. 8 the strands (E) tend to decline slightly with respect to the line X—X perpendicular to the advancing direction of the sealing sheet 3. In the finished garment such as a diaper the strands (E) incline with respect to the width of the base cloth. This inclination of strands has no influence upon the gathered effects but the appearance becomes poor. As commodities the quality is degraded. To avoid the spoiled appearance the method illustrated in FIGS. 9 and 10 is adopted:

There are provided upper and lower stages of conveyor belts 23c (23e) and 23d (23f) at each side, having no pins thereon. In addition there are provided auxiliary belts 26a (26b) and 26c (26d) which keep contact with the belts 23c (23e) and 23d (23f). Under this arrangement the strands (E) are pressed by the auxiliary belts 26a to 26d against the conveyor belts 23c to 23f during transportation.

Now, suppose that the speeds of the belts 26a and 26b be Va and Vb, and that those of the belts 26c and 26d be Vc and Vd. The belts 23c to 23f and 26a to 26d move at the following speeds:

Va=Vd

Vb=Vc

Va<Vc

Under this arrangement the speeds of the elastic strands (E) become different between the upper stage and the lower stage. That is, the strands (E) pressed between the belts 23c and 26a tend to be slower in movement than those pressed between the belts 23e and 26b. Those pressed between the belts 23d and 26c tend to be faster than those pressed between the belts 23f and 26d. By differentiating the speeds of the elastic strands between at the upper and lower stages and also between one side and the other side the declining strands are caused to straighten up, that is, they become perpendicular to the moving direction of the sealing sheet 3. To secure the straightening-up, the values of the speeds Va to Vd must be calculated from the rotating speed of the rotary arm 27.

When a single finished elastic strand (E) is supplied from the arm 27, the speeds Va to Vd should be:

$$Va = 2N \cdot P \tag{1}$$

$$Vd = 2N \cdot P \tag{2}$$

$$\frac{Va}{\iota} = \frac{Vc}{\iota + P} \tag{3}$$

$$\frac{Vb}{\iota} = \frac{Vb}{\iota + P} \tag{4}$$

$$Va = Vd = a \cdot S \tag{5}$$

The equations (1) to (5) are rearranged as follows:

$$Va = Vb = 2N \cdot P = a \cdot S$$

$$Vb = Vc = \frac{\iota + P}{\iota} (2N \cdot P)$$

wherein

Va to Vd: the speeds of the auxiliary belts 26a to 26d;
N: the r.p.m. of the arm 27;
P: pitches;
$\iota$: the distance from the point where the elastic strands start to wind up the belts 23c (23e) up to the point where the tape members are nipped;
a: the gathered width;
S: the number of diapers produced per unit hour.

In the illustrated embodiment the strands (E) are supplied line by line by means of the arm 27, but it is also possible to supply and wind several strands (E) at one time.

$$Va = Vd = 2 \cdot n \cdot N \cdot P = a \cdot S$$

$$Vb = Vc = \frac{\iota + nP}{\iota} (2 \cdot n \cdot N \cdot P)$$

In this way the elastic strands (E) are arranged in parallel with the width of the sealing sheet 3, thereby avoiding an ugly appearance having inclined strands.

Figure 11:
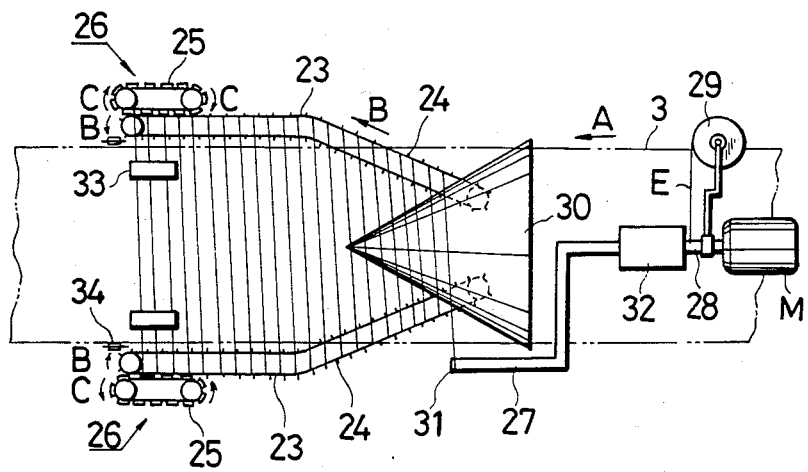
FIG. 11 is a diagrammatic plan view showing another modified version of the arrangement for carrying out the present invention.
Figure 12:
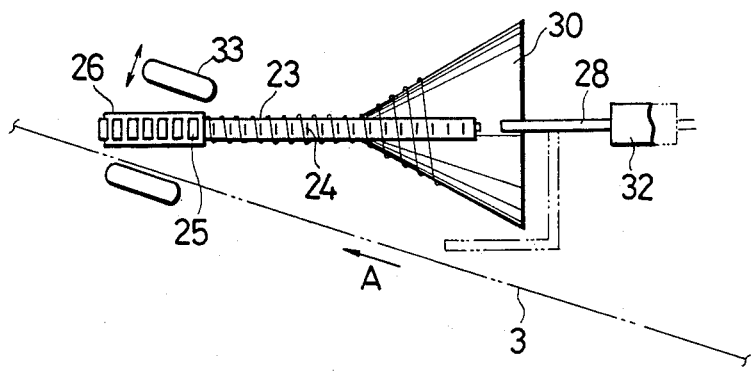
FIG. 12 is a diagrammatic side view of the arrangement of FIG. 11.

Referring to FIGS. 11 and 12 a modified version of the method according to the present invention will be described:

For illustration purpose the sealing sheet 3 is depicted as having inclining strands (E). There are provided a pair of conveyor belts 23 alongside the opposite edges of the sealing sheet 3, each belt 23 being bent inwardly beginning at its middle portion, and moving in the direction of arrow (B). The belts 23 are provided with pins 24 intended to space one strand from another. The belts are of a type, such as timing belts, which are available in the market. The reference numeral 26 denotes a pair of auxiliary belts arranged alongside the respective conveyor belts 23. Each auxiliary belt 26 is provided with pads 25 spaced at constant intervals, which pads are intended to fit in between one pin 24 and the next. The auxiliary belts move in the direction of arrow (C).

There is provided an arm 27 which rotates around the two conveyor belts 23 by means of a motor (M). The arm 27 is provided with a supporting shaft 28. The reference numeral 29 denotes a winder which rotates in accordance with the rotation of the arm 27. The elastic strands (E) are supplied from the winder 29. The arm 27 includes an outlet 31 through which the strands (E) are pulled out. The supporting shaft 28 is provided with a device whereby the strands are tightened up. The reference numerals 33 and 34 denote press members for the strands (E) and rotary cutters, respectively.

In operation, the sealing sheet 3, the belts 23, and the auxiliary belts 26 are driven in the respective directions (A), (B) and (C). At the same time the arm 27 is rotated by the motor (M). The strand (E) is supplied from the winder 29, and placed on the belts 23 at the intervals provided by the pins 24 of the belts 23. In FIGS. 11 and 12 the reference numeral 30 denotes a conical guide member by whose axial position the length of the strand (E) to be wound in a given turn of arm 27 is determined. In this way the strand (E) is conveyed, and by being pressed by the belts 23 and the auxiliary belts 26 it is transferred to the sealing sheet 3 while keeping the intervals set by the pins 24.

The sealing sheet 3 is previously coated with an adhesive across the width. The strand (E) held by the two belts 23 and 26 is placed in contact with the adhesive-coated zones on the sealing sheet 3, and then the press members 33 are descended to apply pressure to the strand (E). At this stage the rotary cutters 34 cut the end portions of the strand (E) which are free from the pressure. Preferably each press member is provided with a sheet of releasable paper or coated with a silicone film so that it is readily released from the adhesive surface of the sealing sheet 3.

Figure 13:
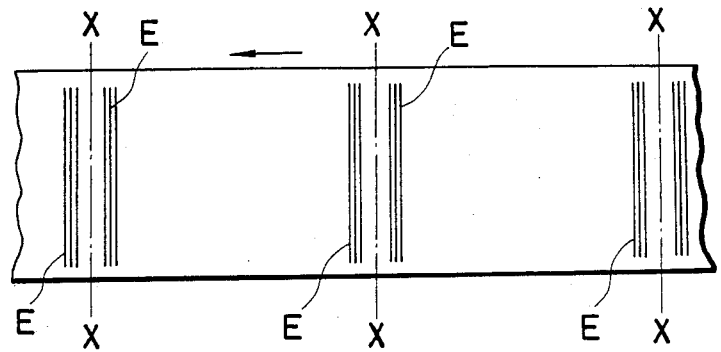
FIG. 13 is a diagrammatic plan view showing a further modified version of the arrangement for carrying out the present invention.

The intervals between one strand unit and the next include a long one and a short one as shown in FIG. 13, wherein the long interval is between the two strand units in the same garment whereas the short one is between a strand unit in one garment and a strand unit in the next garment with the cutting line X—X interposed therebetween. To achieve the difference in the intervals it is required that the belts 23, 26 and the auxiliary arm 27 are intermittently driven by using a step motor, such as a servomotor.

Figure 14:
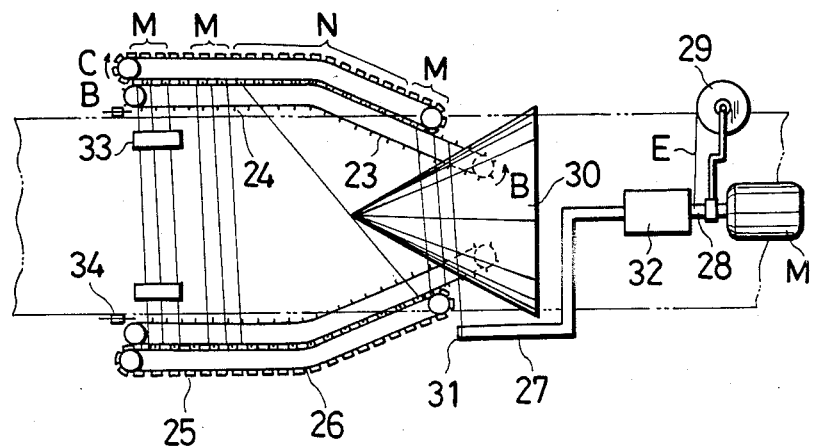
FIG. 14 is a diagrammatic side view of the arrangement of FIG. 13.

FIG. 14 shows another modified method, which has basically the same structure as that shown in FIGS. 11 and 12:

Under this method the strand (E) is previously wound around the conveyor belts 23 at the same intervals as those on the sealing sheet 3, and the speeds of the conveyor belts 23 and auxiliary belts 26 are controlled to be equal. In this case it is not necessary to drive them intermittently, thereby eliminating the necessity of employing a complicated belting system. It is necessary to rotate the arm 27 at an increased speed when the winding of the strand is in progress for portions (M) of the belts 23, and at a decreased speed when it is for a portion (N) thereof. The differentiating speed of the arm 27 is achieved by using a step motor.

What is claimed is:

1. A method of incorporating elastic strands in a garment, the method comprising the steps of:
    coating an adhesive on a base material of a moving garment so as to form adhesive zones at certain intervals;
    moving elastic strands in parallel along the surface of the base material in the moving direction thereof wherein the elastic strands are caused to advance at controlled intervals during the movement of said base material;
    fixing tape members to the opposite ends of the strands in their stretched state;
    cutting the strands at said opposite ends; and
    fixing the strands in their stretched state to the base material by placing said tape members on said adhesive zones,
    wherein the strands are stretched along the width of the base material.

2. A method of incorporating elastic strands in a garment, the method comprising the steps of:
    coating an adhesive on a base material of a moving garment so as to form adhesive zones at certain intervals;
    moving elastic strands in parallel along the surface of the base material in the moving direction thereof wherein the elastic strands are caused to advance at controlled intervals during the movement of said base material;
    differentiating the moving speeds of the opposite ends of the strands such that the ends are aligned in a direction transverse to the moving direction;
    fixing tape members to the opposite ends of the strands in their stretched state;
    cutting the strands at said opposite ends;
    fixing the strands in their stretched state to the base material by placing said tape members on said adhesive zones,
    wherein the strands are stretched along the width of the base material.

* * * * *